United States Patent
Alravvi et al.

(10) Patent No.: US 12,207,607 B2
(45) Date of Patent: Jan. 28, 2025

(54) DATE PALM POLLINATOR AND POWDER DISPERSER FOR HIGH TREES

(71) Applicant: Omar Alravvi, Istanbul (TR)

(72) Inventors: Omar Alravvi, Istanbul (TR); Musaab Omar Mahmood Al-Rawi, Istanbul (TR); Osama Mahmood Al-Rawi, Istanbul (TR)

(73) Assignee: OMAR ALRAVVI, Istanbul (TR)

( * ) Notice: Subject to any disclaimer, the term of this patent is extended or adjusted under 35 U.S.C. 154(b) by 892 days.

(21) Appl. No.: 17/042,823

(22) PCT Filed: Mar. 27, 2019

(86) PCT No.: PCT/TR2019/050198
§ 371 (c)(1),
(2) Date: Sep. 28, 2020

(87) PCT Pub. No.: WO2020/013780
PCT Pub. Date: Jan. 16, 2020

(65) Prior Publication Data
US 2021/0015059 A1    Jan. 21, 2021

(30) Foreign Application Priority Data
Mar. 28, 2018   (TR) .................................. 2018/04390

(51) Int. Cl.
*A01H 1/02* (2006.01)
*A01G 17/00* (2006.01)
*A01M 9/00* (2006.01)

(52) U.S. Cl.
CPC ............... *A01H 1/027* (2021.01); *A01M 9/00* (2013.01); *A01G 17/00* (2013.01)

(58) Field of Classification Search
CPC .......... A01H 1/027; A01M 9/00; A01G 17/00
See application file for complete search history.

(56) References Cited

U.S. PATENT DOCUMENTS

| 2,117,362 | A | * | 5/1938 | Rose ...................... B05B 11/062 |
| | | | | 222/88 |
| 2,802,302 | A | * | 8/1957 | Yost ........................ A01H 1/027 |
| | | | | 47/1.41 |

(Continued)

FOREIGN PATENT DOCUMENTS

| CN | 201630098 U | 11/2010 |
| CN | 106857234 A | 6/2017 |

(Continued)

OTHER PUBLICATIONS

Translation of KR 101553959 B1 (Year: 2015).*
Translation of CN 106724729 A (Year: 2017).*

*Primary Examiner* — Monica L Perry
*Assistant Examiner* — Brittany A Lowery
(74) *Attorney, Agent, or Firm* — Maier & Maier, PLLC

(57) ABSTRACT

A device that provides in trees pollen and/or insecticide includes: a holding tank; a cover cone connected to the holding tank; a ring sealing the cover cone; a dispensing tube connected to the cover cone; a sleeve cylinder having a top portion receiving a cylindrical bottom portion of the holding tank, and a groove; and an internally extending cone in the holding tank, the cone having a base joined by the cylindrical bottom of the holding tank. A ring in the groove and seals the top portion of the sleeve cylinder with the holding tank; a chamber cylinder having a cylindrical top extension connected to the sleeve cylinder, and a joining cylinder opposite the cylindrical top extension; and an air pump. The air pump has a motor and a fan to receive air via pores through the sleeve cylinder and pump the air to the holding tank.

9 Claims, 14 Drawing Sheets

(56) References Cited

U.S. PATENT DOCUMENTS

| | | | |
|---|---|---|---|
| 3,943,660 A | 3/1976 | Hosaka | |
| 4,751,791 A * | 6/1988 | Al-Rawi | A01H 1/027 47/1.41 |
| 5,052,555 A * | 10/1991 | Harmon | A45C 3/00 190/111 |
| 5,226,567 A * | 7/1993 | Sansalone | B05B 15/30 222/325 |
| 6,925,751 B2 * | 8/2005 | Williams | B05B 15/63 47/1.41 |
| 10,960,528 B1 * | 3/2021 | Velez | A01D 34/78 |
| 2017/0239675 A1 * | 8/2017 | Svendsen | B05B 12/002 |

FOREIGN PATENT DOCUMENTS

| | | | | |
|---|---|---|---|---|
| KR | 101553959 B1 * | 9/2015 | | A01H 1/027 |
| WO | WO-2018051315 A1 * | 3/2018 | | |

* cited by examiner

DATE PALM POLLINATOR AND POWDER DISPERSER FOR HIGH TREES

BACKGROUND OF THE INVENTION

Date palms, cherry trees, almond trees and some other monosexual trees need to transfer the pollen from the male tree to the female tree to give proper fruit. For this process, we collect the male pollen and then transfer it to the female tree. In the natural way, the insects or the air will do the pollination, the output will be poor, on the one hand, and on the other, the need for a large number of male trees results in wastes of space and poor production for date palms and yields little or no fruit, or fruit of poor quality. In cherry trees, we may get some fruit but of low quality.

In particular, we need to collect and dry the male flowers and climb to the top of the palm to put part of the male flower branches in the female flower and connect the group to each other to get a good fertilization rate. We know that climbing high trees requires expert workers, and the presence of thorns in the area of fruits makes the process difficult and expensive.

When using mechanization to facilitate the process of pollination, we need pollen powder for use in the devices. The process includes collecting male palm flowers and drying them in dry, shaded areas and then taking them into special machines that collect the pollen and then isolate, by cyclone, the powder alone or after the addition of other expander materials. The process of collecting and storing pollen is difficult, making it relatively expensive. There is difficulty when separating it by farmers and the waste is high, and so it is necessary to apply a solution to this problem for anyone who wants to use modern equipment in pollination.

One of the important points in palm pollination is to reduce the amount of pollen we need for each palm without reducing fertilizing rate. Most of the presently used equipment is very wasteful and the results of the process are not commensurate with the great waste of pollen, which affects the cost of the product.

To make manual pollen transfer easier, therefore, pollinators are used. Some pollinators still require climbing up the tree, like the so-called American and Japanese pollinators, for example. Some of them need heavy machinery or compressed air, like those sold under the marks Al-nahren, Homribi and Baghdad, for example. Some of them are difficult to use in other ways, especially in raising to female flowers at the top of a very high tree.

The inventor named herein has, therefore, also invented pollinators identified as Mosa'ab, Mahmood and Osamah Pollinators to try to avoid the described disadvantage of the other above-identified pollinators. Thus, these require no heavy machinery and no compressed air. They are also cheap and can be raised to the tops of high trees easily. They are also easy to operate.

The Mosa'ab Date Palm Pollinator has a long, graduated aluminum carrying tube. On an upper end of the carrying tube, there is a small cylindrical container for male pollen with a cone-shaped lower part connecting it, point-down, to a horizontal, small-diameter tube, transverse to the carrying tube, for funneling the pollen thereinto. The small-diameter tube is connected at one end to the lumen of the carrying tube and is open at the other end, which projects from the container about 3 cm to allow the pollen to go out. The lower end of the carrying tube has a small bulb pump of about 50 cc capacity. For use, the carrying tube is grasped by hand to position the open end of the small-diameter tube at a female flower. The bulb is then squeezed to pump air into the lumen of the carrying tube and, therefrom, to the connected end to the small-diameter tube to push the pollen dropped thereinto from the container out onto the female flower for pollination.

The Mahmood Date Palm Pollinator has the same carrying tube. Its cylindrical container on one end thereof for pollen also has a cone in its lower end, but it is directed point-upward and inside the container with small bores about its base circumference where it is attached to the cylinder and communicates with the lumen of the carrying tube. The other, upper end of the cylinder is closed by a stopper having ½ cm small-diameter tube 120 cm long passing through it so that its lumen is connected to the lumen of the cylinder. The other lower end of the carrying tube is again connected to an air pump.

Any type of air pump may be used such as, for example, an insecticide sprayer pump. In use, air from the pump passes into the carrying tube, from the carrying tubes into container, through the pollen in the container into the stopper-held tube in the top of the container and then to the female flower, entraining some of the pollen from the container.

The Osamah Date Palm Pollinator is the same as the Mosa'ab, with two differences. First it has a 100 cm long tube extending vertically from the open end of the horizontal tube. Its action is to take the pollen to the female flowers. Second, it has an electric air pump on the other, lower end of the carrying tube in place of the bulb pump previously described. The electric pump works on two, dry, 1.5 volt batteries to give enough low-pressure air for pollination work.

In all three of Applicant's prior pollinators, a mix of one part extracted pollen to 10 parts of fine flour is usable in the container.

The disadvantages of the Mosa'ab pollinator are slow discharge of the pollen mixture, linking in the leaves and leaflets of the female palm tree too easily and the possibility of clumping of the flour mixture inside. Its advantages are its light weight, that it does not need compressed air, and that it can reach to 12 m high.

The disadvantages of the Mahmood Pollinator are that it needs repeated pumping and that the torque of tree contact with the upper, stopper-held, small tube can break it, because it cannot bend. Its advantages are that n it has a very rapid (fastest) discharge of the pollen mixture, that it can reach to 14 m high, that it will not link in the leaves and leaflets of the female palm tree, that it is more economical in its use of the pollen mixture and that the pollen mixture does not clump inside it.

The disadvantages of the Osamah Pollinator are that it is too easily blocked by clumps of the pollen mixture and that its output of the pollen mixture is irregular. Its advantages are that it does not need repumping because it works on a battery and that it does not link in leaves and leaflets of the female palm tree.

All of applicant's prior pollinators have a further great advantage in that each can be carried easily by hand between the trees and do not need big, difficult, additional machinery. Also, they have the air power from below and the pollen in the opposite, upper end. That means no loose pollen in the long carrying tube and no heavy part in the upper end. (If the diameter of the carrying tube is 3 cm, this means a volume in 10 m of about 7000 cc. This means a loss from use of 7000 cc of pollen saturated air if the pollen were air-entrained at the lower end of the carrying tube. Such substantial pollen loss is shown to be realistically avoided by comparison to the 95 cc volume of the small-diameter tube of the Mahmood Pollinator.)

The inventor named herein has, therefore, also invented a pollinator submitted as the date palm pollinator of U.S. Pat. No. 4,751,791A and issued by the United States of America on 18 Feb. 1987, for which we found the following.

1. We cannot determine the dose of pollen for each palm as seven liters of compressed air in the tube will continue to flow after leaving the palm, which leads to the loss of a quantity of valuable pollen. In addition to that, pollen emerges from the top of the tube, so, no dose is specified.
2. Battery consumption is high. Because we use a relatively large air pump, making the use of a small rechargeable battery is not suitable.
3. The process of filling the reservoir tank of the pollinator is relatively difficult because the filling was from the small opening.
4. The small holes in the bottom of the tank may close with wet pollen and cannot be cleaned because the tank is closed, and there was no idea of use as disposable.
5. It is not used with insecticides because the tank will be contaminated, difficult to clean and has no alternative tank.
6. The bearing tube needs accurate manufacturing to prevent air leakage, forcing us to use tape around elongation areas.
7. Although the invention was sufficient for pollination, it was lacking the device for isolation of pollen. It is simple at the same level of simplicity of the pollinator so that farmers in far areas are self-dependent to get the pollen.

The disadvantages that made us put the pump down no longer exist, because the evolution that has occurred on the production of pumps makes them small, light and powerful. So we were able to put the pump at the top with very little side effect.

It is, therefore, an object of the invention to provide a plant duster and, more particularly, a duster for date palm pollination which avoids at least some of the disadvantages and retains most of the advantages of those described.

BRIEF DESCRIPTION OF THE DRAWINGS

Prior and preferred embodiment of date palm pollinators which illustrate, but do not limit the invention are shown in the drawings, wherein.

REFERENCE NUMBERS TO HELP DESCRIBE THE INVENTION

Figure 1:
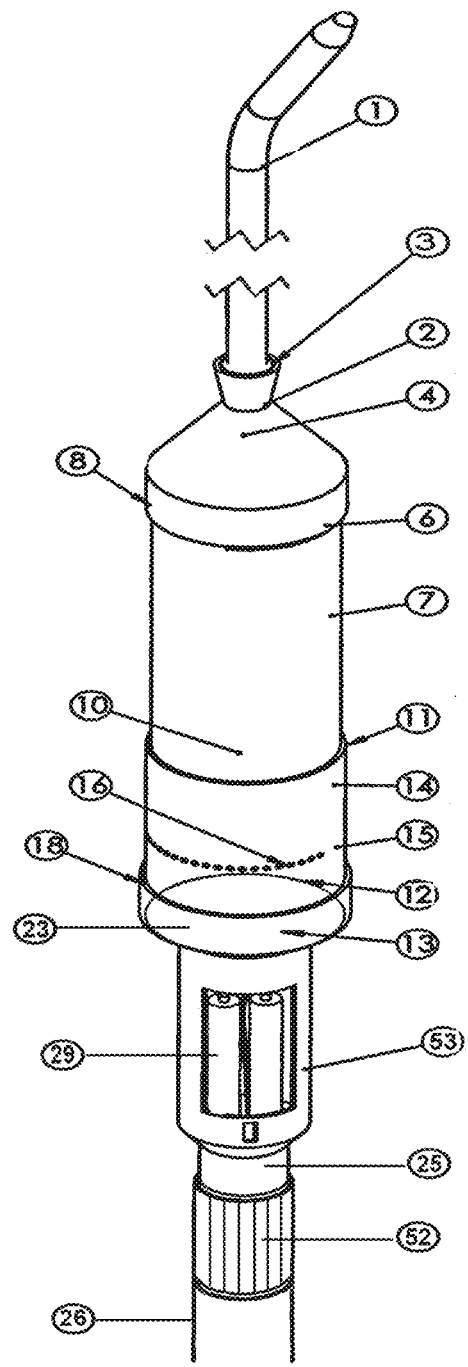
FIG. 1: Front view of the upper part of the device for pollination.
Figure 2:
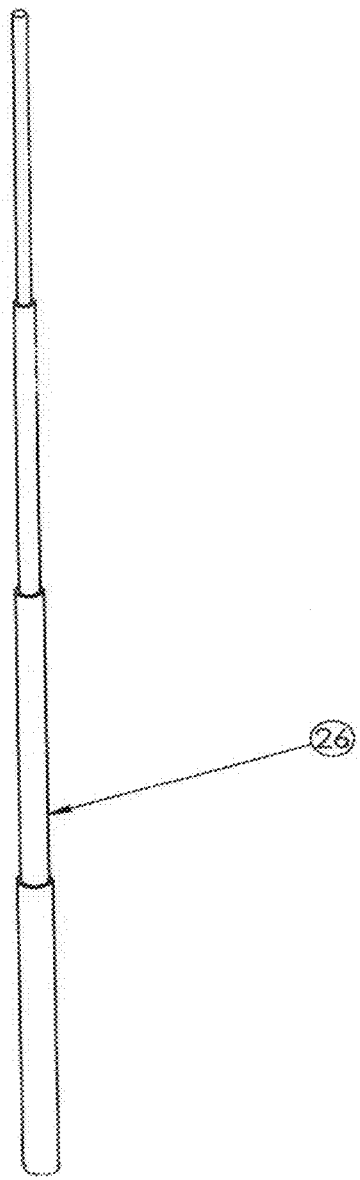
FIG. 2: Front view of the telescopic carrying tube.
Figure 3A:
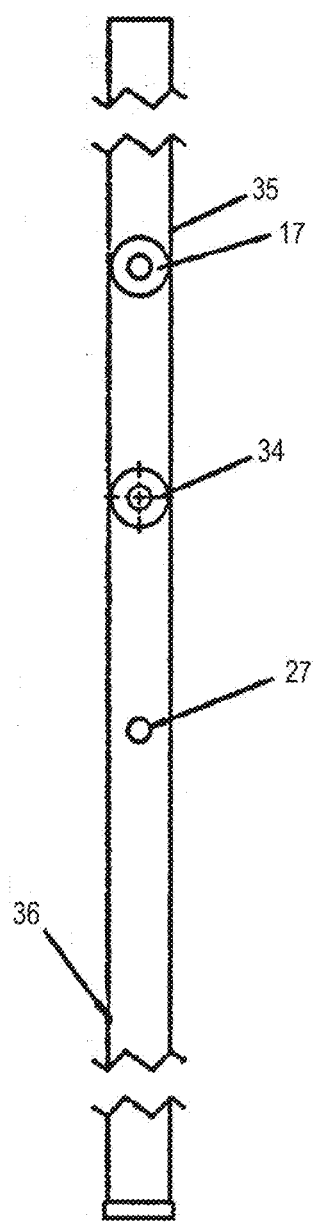
FIG. 3a: Front view of the lower section of the carrying tube and remote control system.
Figure 3B:
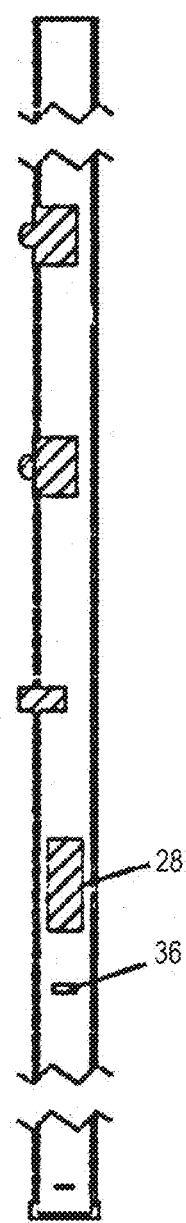
FIG. 3b: Side view of the lower section of the carrying tube and remote control system of the pollinating device.
Figure 4:
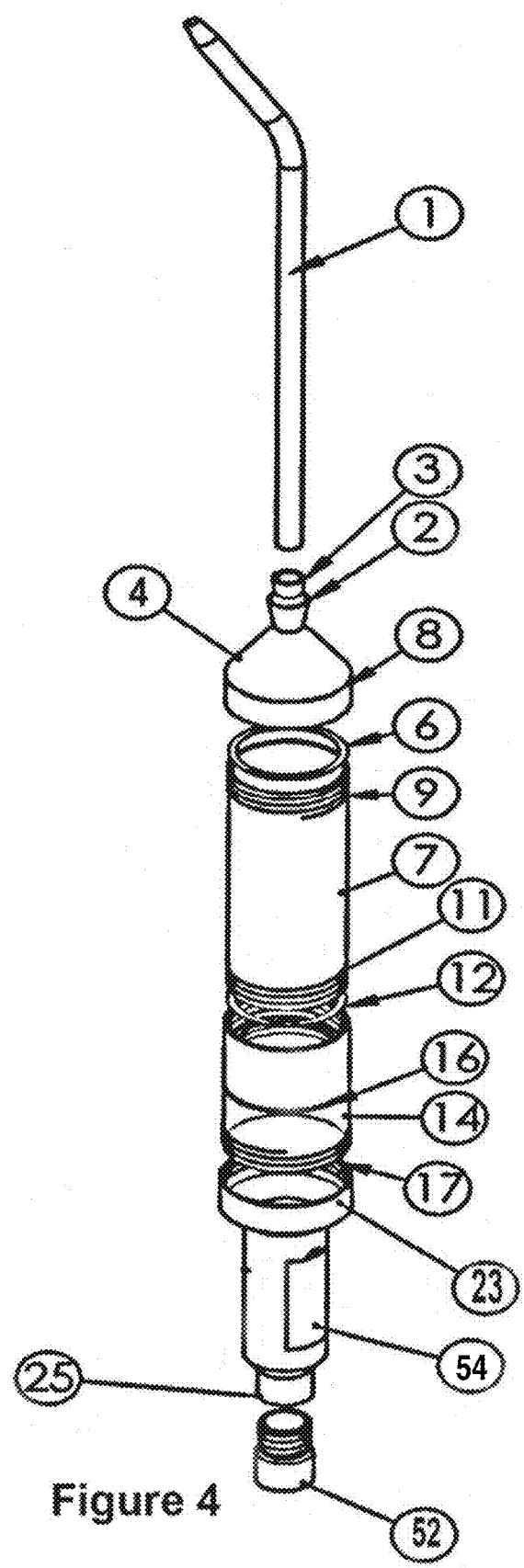
FIG. 4: Top view of the upper part of the device which provides pollination.
Figure 5:
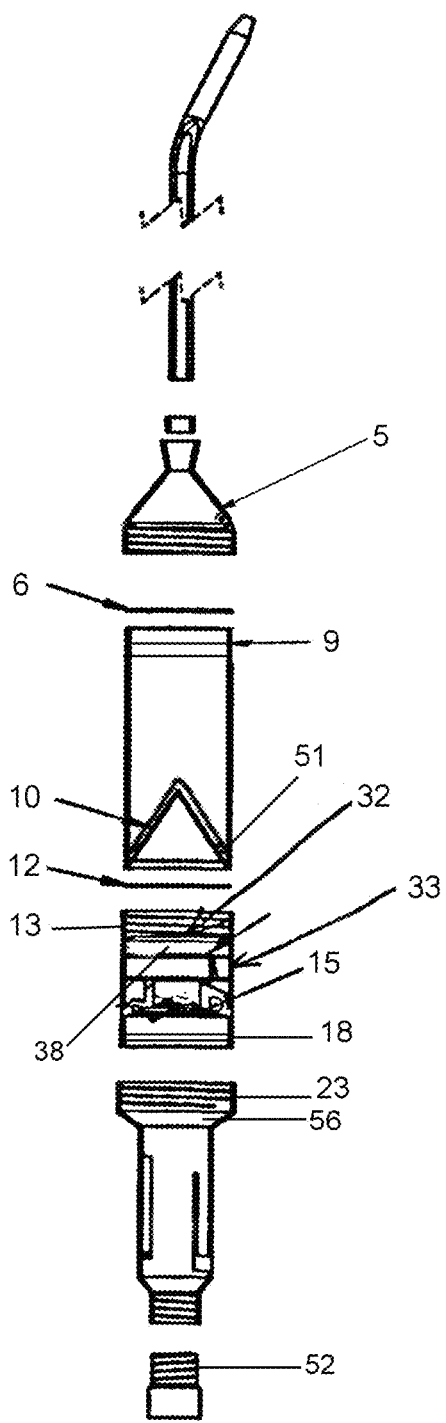
FIG. 5: Side view of the upper part of the pollinator.

1 Dispensing Tube
2 Truncated hollow end cone.
3 Rubber stopper.
4 Truncated hollow cover cone.
5 Groove.
6 Rubber ring.
7 Pollen holding tank.
8 Cylinder extension.
9 Threads.
10 Hollow internally extending cone.
11 Threaded end.
12 Rubber ring.
13—Threaded screw.
14 Sleeve cylinder.
15 Air pump.
16 Pores.
17 Speed control switch.
18 Threaded screw.
19 Air pump fan.
20 Compact cylinder.
21 Motor.
22 Cable.
23 Cylindrical power cylinder top extension.
24 Truncated hollow cone.
25 Hollow threaded joining cylinder.
26 Telescopic carrying tube.
27 Power switch.
28 Battery pack.
29 Chargeable batteries.
30 Supporting wings.
31 Cylindrical motor housing.
32 Groove for rubber ring.
33 Tubing hole
34 Timer system.
35 Hard plastic carrier tube.
36 Charging slot.
37 Cloth bag.
38 Space.
39 Plastic sheath pipe.
40 Cable.
41 Handle.
42 Hands.
43 Cover.
44 Yarn.
45 Male flower cluster.
46 Grinding mill.
47 Bag zipper.
48 Holder.
49 Pollen collecting bag.
50 Pollen tank cover.
51 Pores.
52 Plastic end piece of the carrying pipes.
53 Power cylinder containing batteries and electronics.
54 Battery cover.
55 Charging port.
56 Truncated hollow reduction cone.
57 Bag.
58 Transparent plastic tube.

DISCLOSURE OF THE INVENTION

The new date palm pollination device consists of a dispensing tube (1) of good plastic with an internal diameter of 7 mm and a length of 90 to 100 cm with a curve in the last 10 cm to pass the mixture of flour and pollen to the palm.

At one end and before 4 cm from the end there is a 2.5 cm rubber stopper (3) helping the tube (1) to flexibly fix on a truncated hollow end cone (2) which is connected to the top of a truncated hollow cover cone (4), which serves as the cover of the pollen mixture holding tank (7).

The pollen tank (7) consists of a cylinder with a diameter of 6-8 cm and 16 cm long and open from the top where it is connected to the cover cone (4) by its threads (9). The cylinder extension (8) is connected to the truncated hollow cone cover (4), which is connected by the end cone (2) into which the rubber stopper (3) is inserted.

There is a rubber ring (6) placed so when the threads (9) are connected to the cylinder extension (8) the rubber ring will prevent air leakage from the tank.

Tank (7) is closed from the bottom with an internally extending cone (10). Its apex is directed upward and its base is joined to the cylindrical end of the tank (7), the thickness of this cone is 2 mm at 5 mm from its point of contact with the cylindrical end of the tank (7). 40 holes (pores 51) of 1.5 mm diameter are in a mean horizontal of the base of the internally extending cone (10) and the length of each pore is more than 2 mm and this trend prevents the mixture powder from leaking from the reservoir tank (7) to the cavity below.

The tank (7) has a lower threaded end (11) connected to the sleeve cylinder (14), and a rubber ring (12) is at a groove (32) to prevent leakage of air. The sleeve cylinder (14) is enclosed by a barrier and has a tubing hole (33) that conveys air from the air pump (15) of space (38). The pump enters the air from the pores (16) and the fan (19) installed on the motor (21) The motor is installed in the compact cylinder (20) whose diameter from the outside is perfectly suitable for the sleeve cylinder (14) from inside. There are plates connecting the cylindrical motor housing (31) with the compact cylinder (20). The cylindrical power cylinder top extension (23), which is 2 cm in length, is connected to a truncated, hollow cone (24), which in turn is connected to a power cylinder (53).

Figure 6:
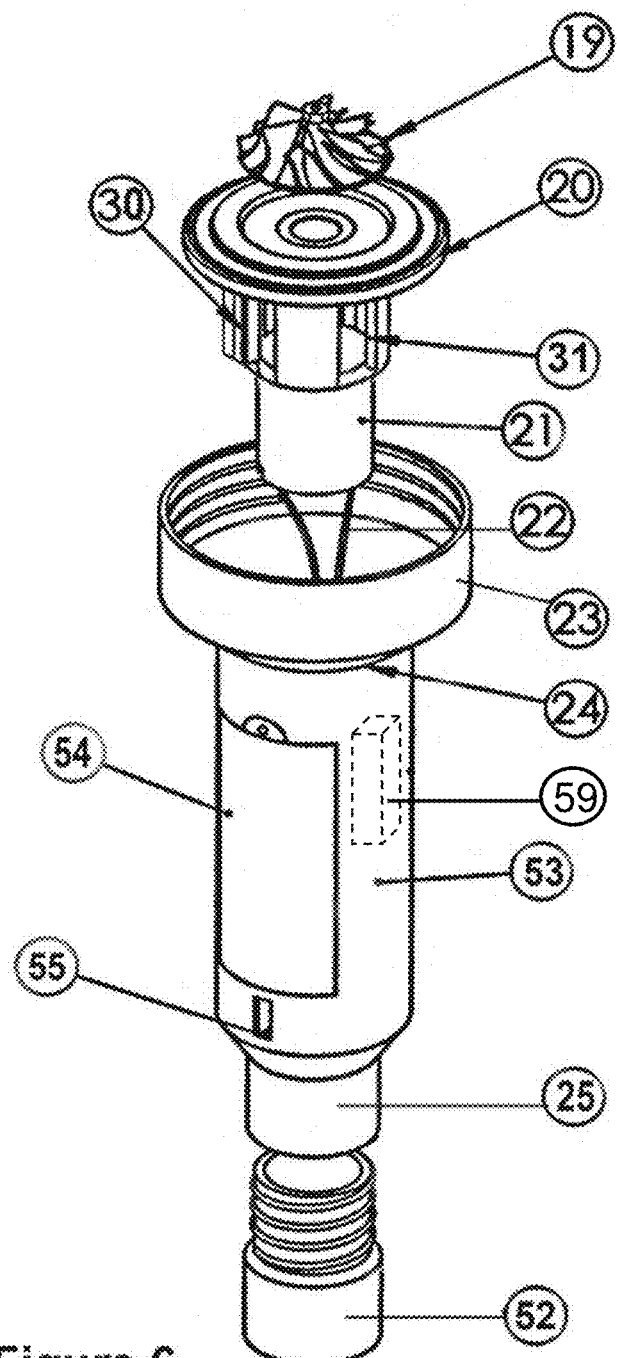
FIG. 6: Front perspective view of the motor and battery container of the pollinator.
Figure 7:
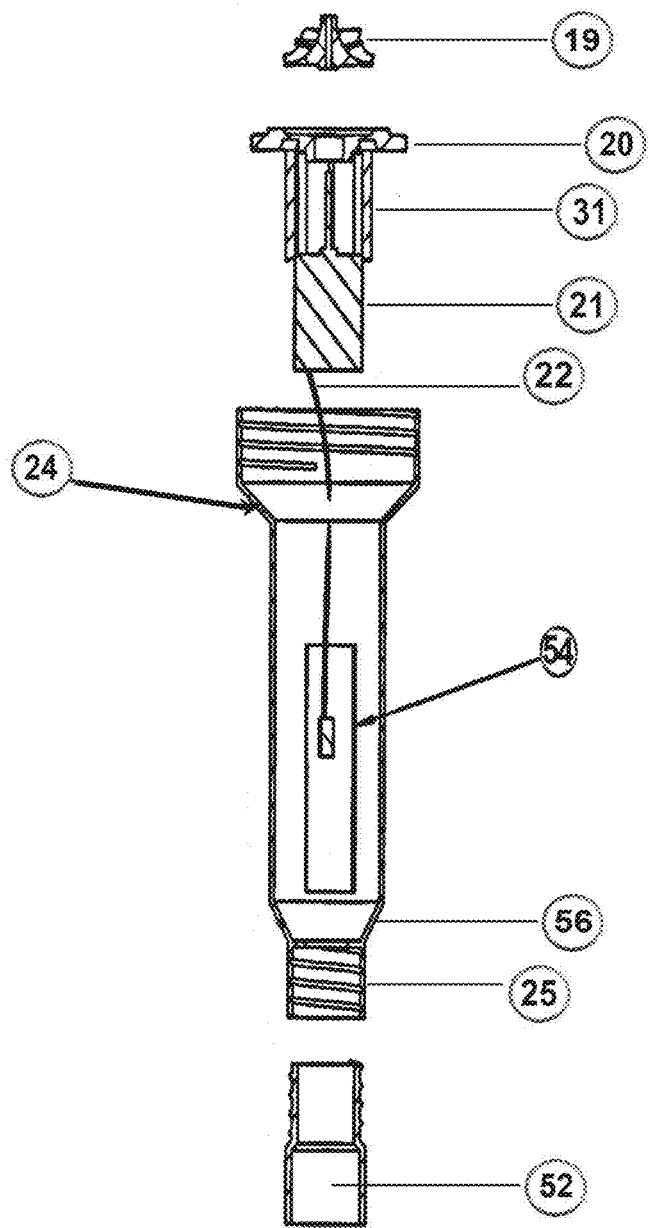
FIG. 7: Side view of the motor and battery container of the pollinator.
Figure 8:
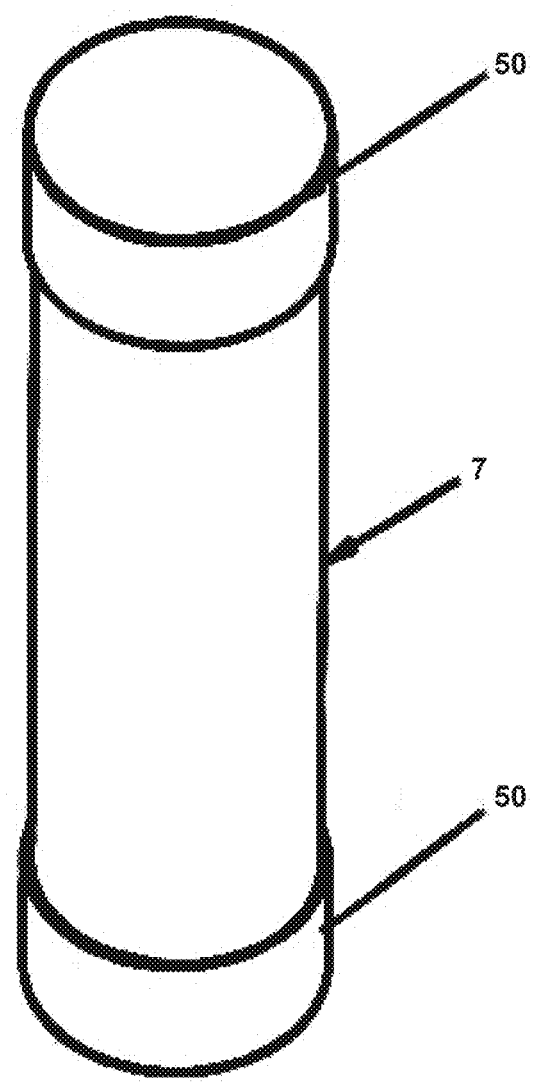
FIG. 8: Front perspective view of the pollen tank of the device.
Figure 9:
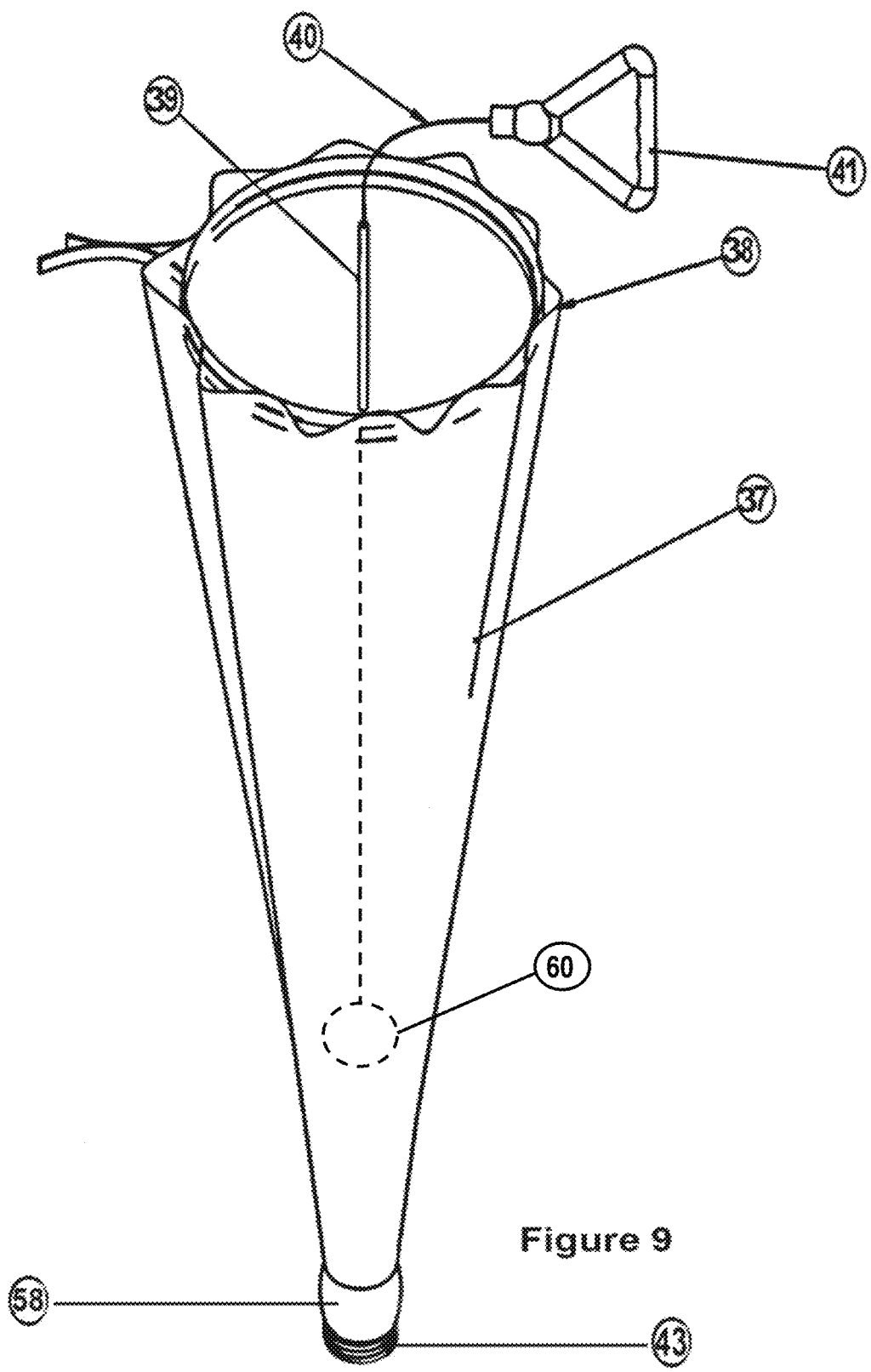
FIG. 9: Front perspective view of the pollen separator.
Figure 10:
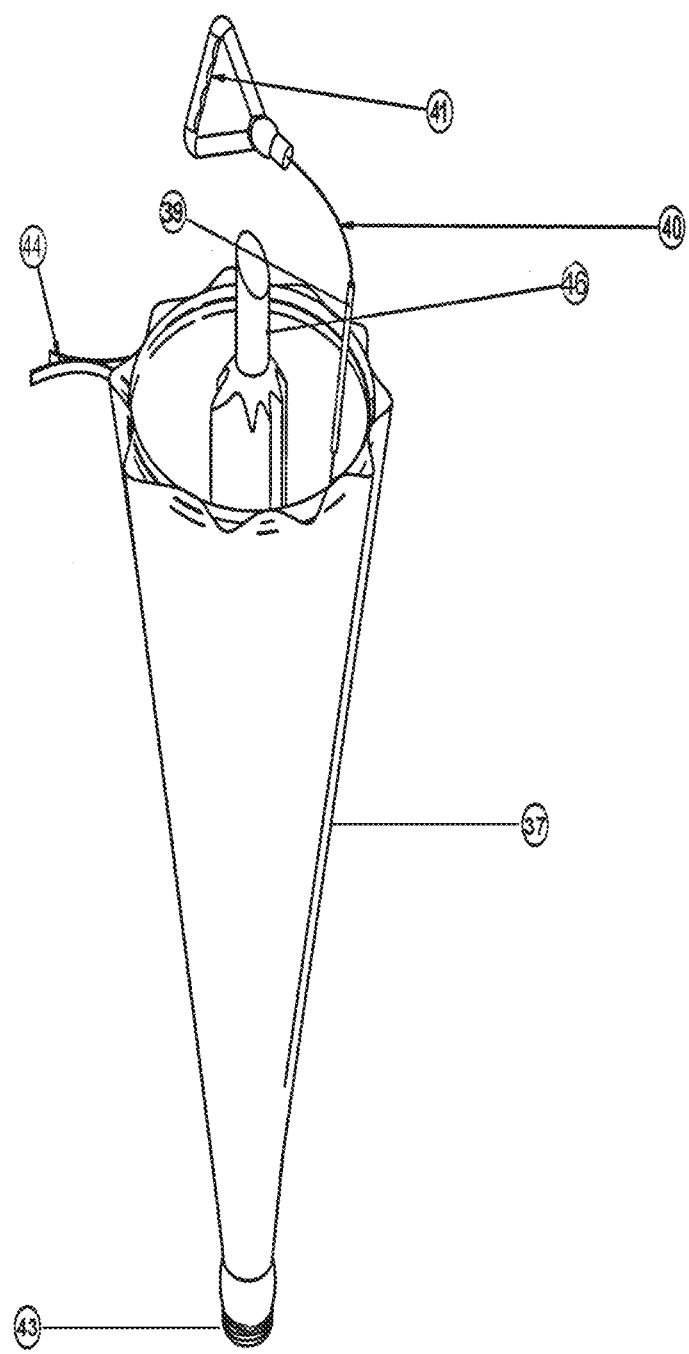
FIG. 10: Front perspective view of the pollen separator on the male cluster.
Figure 11:
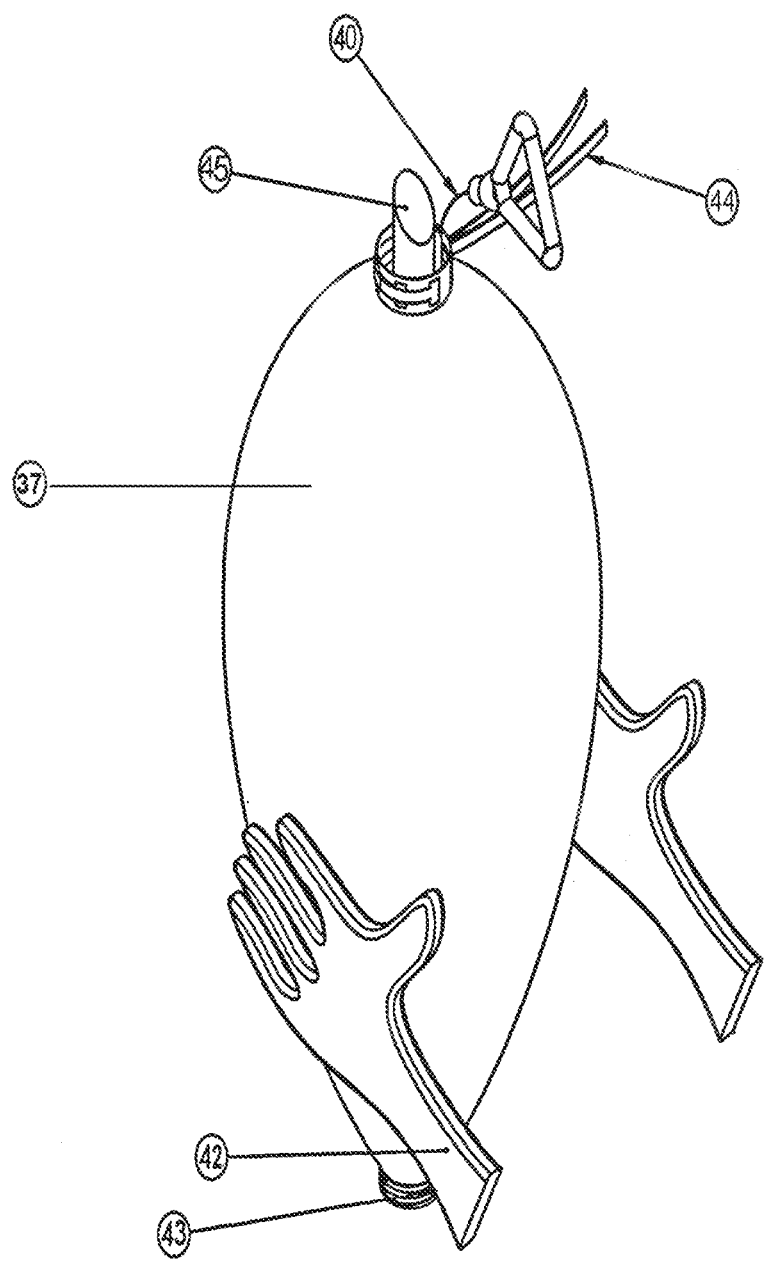
FIG. 11: Front view of the grinder of the male pollen cluster of the device.
Figure 12:
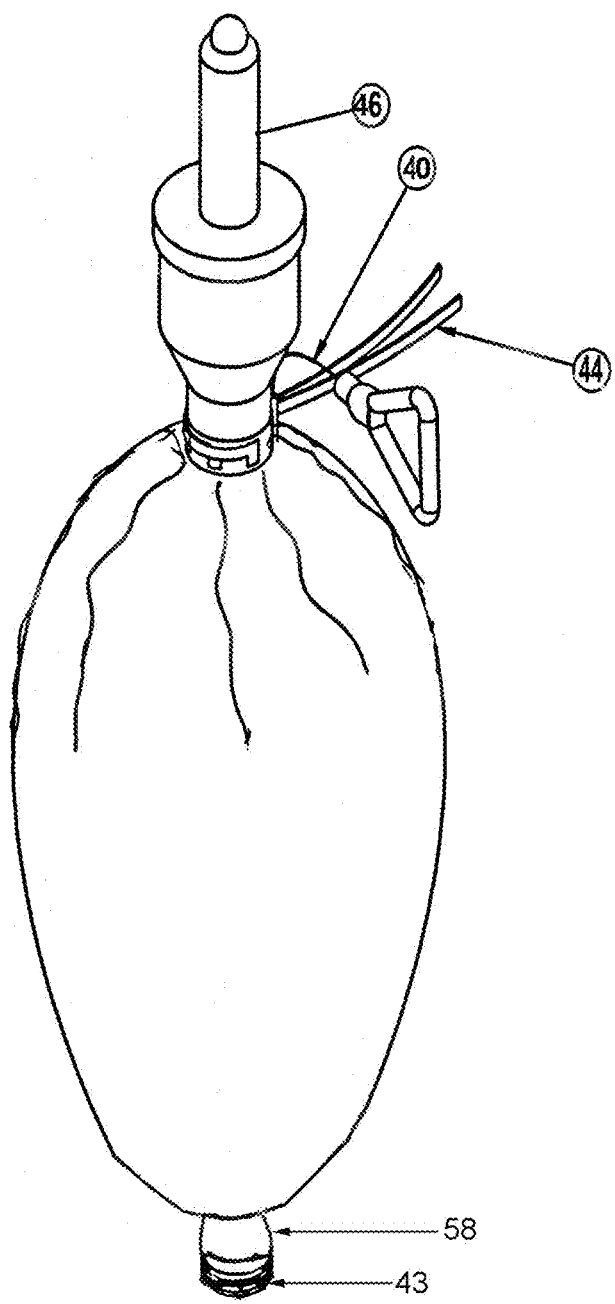
FIG. 12: Front view of the mill grinder of male flowers.
Figure 13:
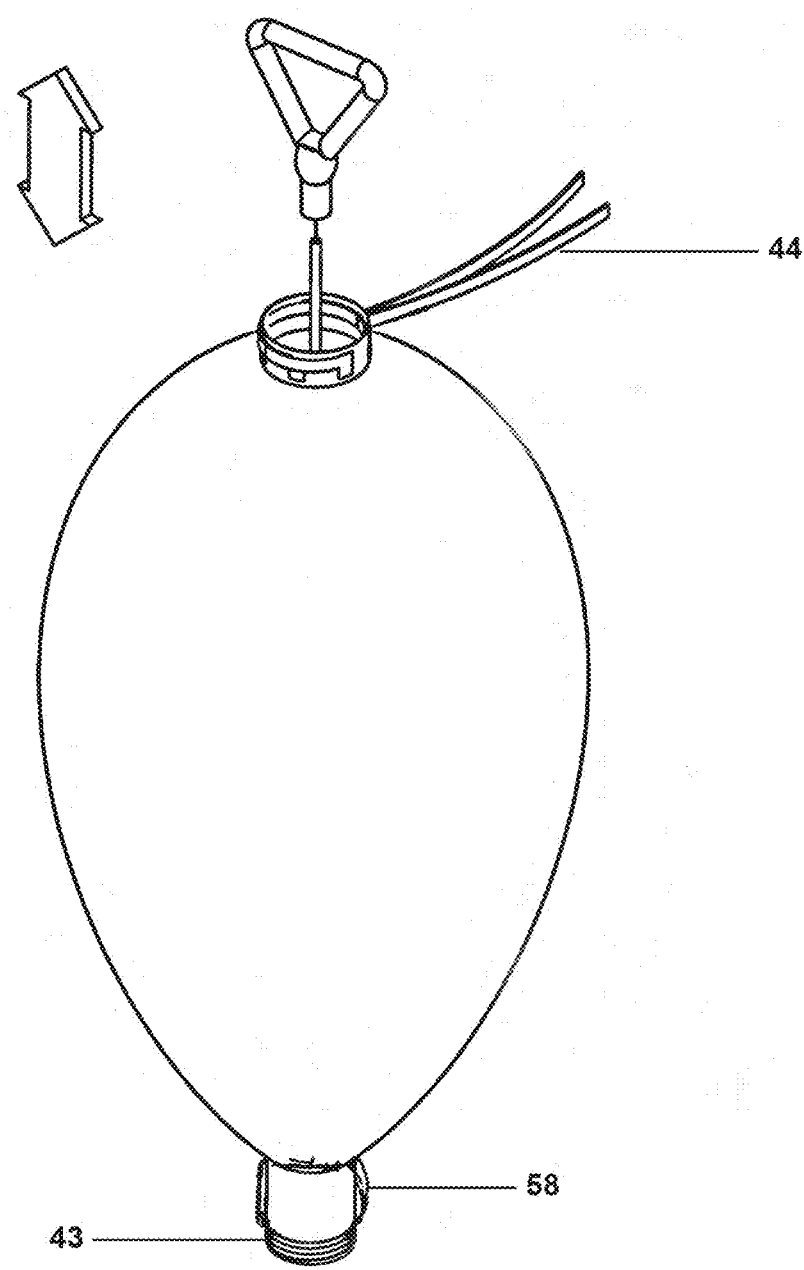
FIG. 13: Front view of the pollen separator.
Figure 14:
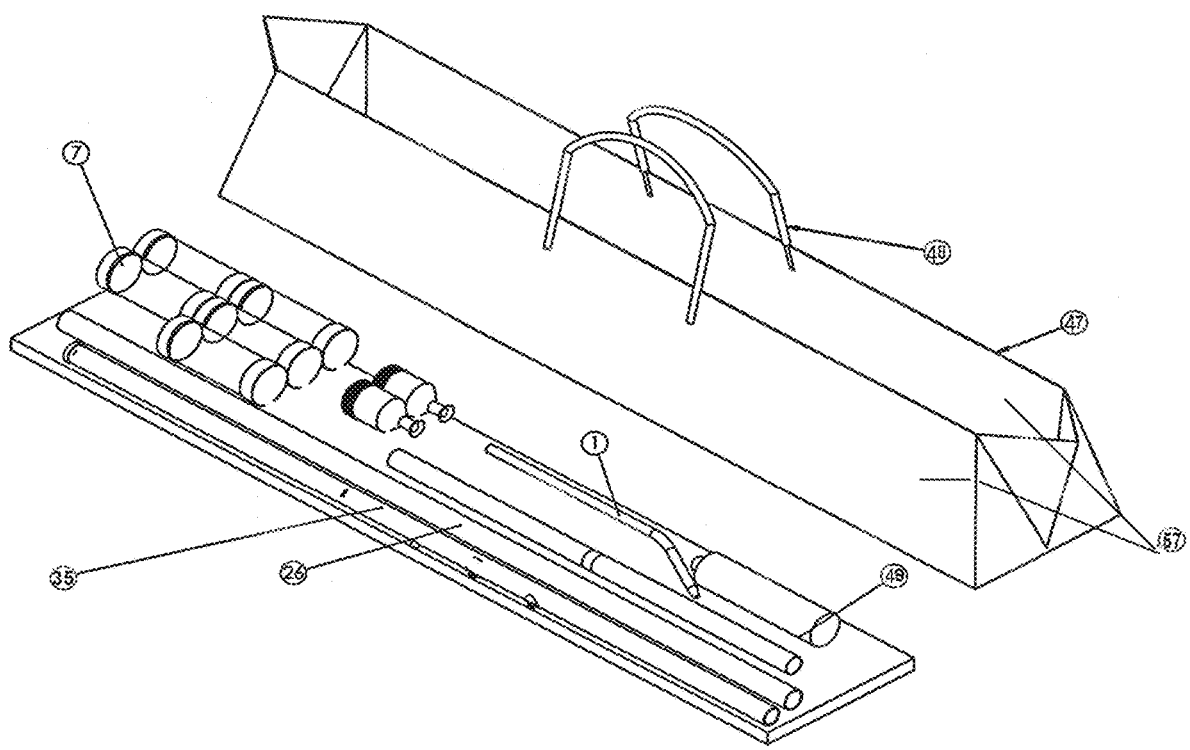
FIG. 14: Top perspective view of the bag and accessories of all the devices.

The power cylinder (53) has a 4-6 cm diameter and is 8 cm long. The power cylinder (53) contains 1-2 batteries (29) with a special electronic system (59), shown in dashed line in FIG. 6, which receives signals from the timer system 34 in the carrying tube (35) to regulate speed and work time. The power cylinder (53) has a battery cover (54) and a USB charging opening 55. The power cylinder (53) is connected to a truncated, hollow reduction cone (56) which is connected to the threaded joining cylinder (25) which connects to the end piece (52) installed on the telescopic carrying tube (26). The cylindrical power cylinder top extension (23) is connected to the power cylinder (53) to be part of the bottom of the pollinator machine.

The telescopic carrying tube (26) consists of four or five pieces as needed, arranged in telescopic relation to each other. The telescopic carrying tube is made from aluminum, and the length of the piece is 120 cm.

The bottom end of the telescopic carrying tube (26) is connected to a hard plastic carrying tube (35) containing a rechargeable battery packs that is sufficient to operate of the remote control system for a whole day before being recharged. The hard plastic carrying tube further includes a power switch (27), a timer system (34), and voltage regulator (17), and further at the bottom there is a charge slot (36) connected to the battery pack (28).

In all the previous pollinators we used a mixture of 20% pollen with a fine flour of 80% mixed well.

The pollen isolation device is composed of a bag made of sieve cloth measuring (3000 openings per square inch), a cone length 70 cm and a base width of the top of 30 cm, tied with a cloth bag (37) in the base, and a length of 85 cm. A plastic sheath pipe (39) with a length of 15 cm and a diameter of 0.4 cm is affixed to the slot of the bag. It is 5 cm extended from the top, through which a 0.15 cm diameter wire (40) and a length of 80 cm is connected to the top with a plastic grip (41). The bottom end of the wire is connected to a coated metal ball (60) of iron with a diameter of 3.5 cm, disposed inside the bag. The bottom of the cloth bag (37) is connected at its lowest point to a clear plastic truncated cone with a diameter of 8 cm (58), closed from below by a threaded cover (43). At the top of the bag at the end there is a thread (44) that tightens the slot of the bag.

To collect the pollen, we place the entire male flower cluster of the male tree (45) into the bag and then rub it until the flowers fall out of the branch. The metal ball drops free to shake the internal sieve bag for many times. After the completion of the process of sieving, the semi-empty flowers come out and are placed into a small mill similar to a black pepper mill with three differences. The first is that the grinding speed is much greater because there is no need for great pressure to crush the fragile male flowers. The power button is not timed but when pressed the mill runs continuously. After the grinding, we sieve it as good as we did before until the last grain of pollen is collected.

The bag 57 is 130 cm long and this length makes it easy to carry in a car trunk or by hand. The telescopic carrying tube (26) can be placed inside the bag, along with the sieve machine, the lower plastic control tube (35) and five pieces of pollen holding tanks (7) which may be filled with insecticide or pollen and sealed with special covers (50) adapted to the tanks (7) from top and bottom.

Two sets of the cover (5), the rubber plug (3), and the dispensing tube (1) can be provided, indicated by red for insecticide and green for pollination. A number of dispensing tubes (1) can be added as spare parts. The bag is closed by a zipper (57) and includes two cloth handles (48) for easy carrying. The complete bag weighs approximately two kilograms if the pollen tanks are empty.

We may add to this bag a small brush to clean the tank after use.

Comparison with Prior Art

As stated in the U.S. Pat. No. (U.S. Pat. No. 4,751,791 A), all the pollinators that we invented and tested, which are Musab, Mahmoud and Osama, showed problems in the application and we improved them to reach the previous US Patent. But after a long time of application we received the observations, and studied carefully, we take account of scientific changes and scientific development, we developed our invention, which is not only the development of the patent in the US, but we have added some important accessories that we see necessary to make the pollinator more applicable and useful and we will clarify this as follows.

We changed the aluminum tube (1) into a lightweight plastic tube that was strong enough and cheap, so it could be used once or twice because the fine tube was very difficult to clean. We made the tube (1) enter 4 cm into the tank to prevent the exit of blocks of material where the direction of the air will be reflected before entering the tube.

We also changed the shape of the pollen holding tank (7) which was closed and made it open for easier filling and cleaning or throwing out after use (disposable) in the case of use of toxic insecticide substances or give bad smells. We made it easy to manufacture from lightweight and transparent plastic and for a low cost so that the farmer can dispense it easily. We made covers (50) for the top and bottom so that the material could be kept in the holding tank before reaching the field at the right place for preparation. These tanks (7) can be sold full of insecticide or ready-mixed pollen.

We put a pump (15) under the tank (7) directly so that the exit of the pollen stops from the dispensing tube (1) when the pump stops directly, and so there is no place where the air is compressed and collected as in the previous pollinator, as the size of the carrying tube is 7 liters and when the air under pressure, it will contain twice that amount, leading to the continuity of the exit and loss of pollen or insecticide materials.

The pump is very light and has little effect on the weight gain. We controlled the air with two rubber rings while in the previous pollinator there was a lot of air loss in the joints of the carrier tube (26) and in the connection areas of the tank with the carrier tube. We controlled the pump with two systems, the first we can increase its speed by increasing voltages to be suitable for some relatively dense insecticide materials. We put a temporary timer to determine the operating time in seconds sufficient for each palm to prevent the loss of any amount of precious pollen.

The batteries and the control system at the bottom and at the top can be easily separated and taken for recharging as one piece, it has a charger socket for charging at night and the charger is enough to operate for a full working day. The telescoping carrying tube can be aluminum or plastic and the fittings are fixable at any length we need.

The pollen separator device is very simple, consisting of a sieve bag into which is placed the male date palm cluster, the thread (44) is tightened and then the bag is rubbed by the hands to cause pollen to fall from the male flowers.

The ball (60) moves by withdrawing the metal wire (40) connected to the catcher (41). The pollen is then taken into the bag and collected in the transparent tub (58). The empty male flowers, which have a significant amount of pollen, are then collected into the modified black pepper mill and placed in its reservoir tank while pressing the push button. It works continuously, until the button is pressed again, to grind the male flowers, which pass directly to the pollen separator and crushed well. After removing the bran from the inner bag by withdrawing the weight connected to the wire (40) to the maximum extent that possible. The reluctance of the farmer to use the pollinator is due to the lack of access to pollen easily, the machine that used routinely is very large and not for individual use and cost tens of thousands of dollars, which is produced on a large scale for marketing, and the pollen is very expensive so the presence of a device to isolate pollen became a same necessity as the pollinator, and we considered it part of the invention.

It is possible to place flour directly in the same way or prepare it alone, mix well all 4 flour weights to the weight of pollen, open the cover (43) and free the result of grinding and mixing. It can be stored in a cool place after placing in reservoirs or spare reserve in the bottle of empty drinking water or a special box prepared for that.

The reservoir tank (7) is filled with only to the half from the mixture, the tank is transparent and the material level can be defined. The quantity is sufficient for ten palms. Each palm receives three puffs of different directions to neutralize the impact of the wind. However, it is preferred to examine the presence of pollen for every 5 palms and trying to fill it to the half.

The parts of pollinator are connected by connecting the pump to the bottom end (18) and then connected to the tube (26). Install the lid (50) on the reservoir (7) and then fix the tube (1) in place, then attach the tank to the pump (15). From the bottom, connect the power set that has been charged before, and after the socket is connected to the socket in the group. The pollinator is ready to work. After the length of the telescopic tube is extended, the speed of the motor is determined by the button and the required time is determined with the timer.

Raise the pollinator to be 30 cm from the center of the palm and a slightly higher level than the female expeditions of the palm. With one push the pollen reaches the target, pull it out of the palm and then turn a third of the circumference around the palm and we do another blow, as the first time and after a third of a cycle, the third blow. The palm pollination has been done. This work is repeated weekly. Four or five weeks from the opening of the first flower. Some species need as many as ten times.

In the case of insecticide use, the tank must be filled only half as in the pollination. It is necessary to make sure that the tank is used for the insecticide. The insecticide materials may be pre-filled in the same tank. We only have to lift the two covers (50). Adjust the speed of the motor and adjust the timer on the open time, which is working as long as the button is pressed, and we distribute on demand and product instructions for the material, take all the precautions for the toxic material such as special clothes and masks.

In all cases, direct observation of pollen and other materials by eye remains a good criterion for the device being worked perfectly.

The results of the application showed that one worker can easily pollinate 500 palms per season. The presence of precise standards makes the dose of pollen very ideal and consistent. The waste has disappeared to the extent that the rate of exchange of pollen declined from our previous invention mentioned 40%. The result in comparison with other pollinators is up to one to ten in the amount of pollen consumed.

In small orchards and gardens our invention is the best solution because having an expert to climb to the palm is very difficult. As well as the control of plant disease by fogging is very difficult and requires calling control teams with high cost for a few trees. Accordingly, the use of this invention is cost-effective.

The invention claimed is:

1. A device for providing in trees at least one of pollen and insecticide with a timer for determining a duration of dispensation, wherein the device comprises:

a cylindrical pollen holding tank having a top end and a cylindrical bottom end, the cylindrical bottom end having a same diameter as a diameter of the holding tank;

a cover cone connected to the top end of the holding tank, the cover cone including a bottom end having diameter substantially similar to the diameter of the holding tank so as to couple to the holding tank;

a first ring sealing the cover cone with the top end of the holding tank;

a dispensing tube connected to the cover cone;

a sleeve cylinder having a top end receiving the cylindrical bottom end of the holding tank, and a groove, the sleeve cylinder having a diameter substantially similar to the diameter of the holding tank so as to couple directly to the holding tank;

an internally extending cone in the holding tank, the cone having a bottom end joined to the cylindrical bottom end of the holding tank proximate a bottom edge of the holding tank;

a second ring in the groove and sealing the top portion of the sleeve cylinder with the bottom end of the holding tank;

a power cylinder having a cylindrical top extension connected to a bottom of the sleeve cylinder, and a joining cylinder opposite the cylindrical top extension, the cylindrical top extension having a diameter substantially similar to the diameter of the holding tank and to a diameter of the sleeve cylinder so as to couple to the sleeve cylinder, said diameter of the cylindrical top extension being greater than a diameter of the power cylinder, and the joining cylinder having a diameter less than the diameter of the power cylinder;

an air pump in the sleeve cylinder, the air pump comprising at least one motor and at least one fan connected to a center of rotation of the at least one motor, wherein the air pump receives air via pores through the sleeve cylinder and pumps the air into the holding tank;

wherein the power cylinder comprises a charging port, houses at least one battery with an electronics system, and is closed with a battery cover;

wherein the electronics system receives a signal and activates the motor for a duration according to the signal;

a telescopic carrying tube configured for coupling to the joining cylinder;

a timer system mounted on or within the telescopic carrying tube, wherein the timer sends the signal received by the electronic system and thereby limits the duration.

2. The device according to claim 1, wherein at least one of the first ring and second ring comprises rubber.

3. The device according to claim 1, wherein the cover cone comprises:

a cylinder, disposed at a bottom end of the cover cone and provided with a thread configured for attachment to the pollen tank; and a truncated hollow cone disposed at a top end of the cover cone, and having a rubber piece coupled to a frustum thereof, the rubber piece being adapted to couple to the dispensing tube, wherein a proximal end of the dispensing tube protrudes from the frustum into an interior of the cover cone, wherein the cover cone, the cylinder, and the truncated hollow cone are integrally formed.

4. The device according to claim 1, wherein the telescopic carrying tube comprises:

a first part, formed from aluminum and including a plurality of sections arranged in telescopic relation to each other, an end of the first part configured to couple to the joining cylinder;

a second part comprising a single-piece tube, in which an internal electronics system is disposed, the internal electronics system including a power switch, a time control system, a speed control system, a remote control electronic circuit, a battery pack, and a charging slot are disposed, wherein the motor speed and motor operation time are controllable by the internal electronics system.

5. The device according to claim 1, further comprising a two-part electronic control system, the two-part electronic control system comprising:

a first electronic part comprising the electronics system disposed in the power cylinder, which further comprises an electronic circuit configured to control operation of the motor;

a second electronic part of the electronic system disposed in a single-piece tube of the telescopic carrying tube, and further comprising a timer and an electronic circuit including a speed limiter and a battery;

wherein the electronic system is controllable by one or both of the first electronic part and the second electronic part, and wherein the first electronic part and the second electronic part are controlled by a power switch disposed on the single-piece tube.

6. The device according to claim 1, wherein the holding tank is adapted to be provided separately from the device and prefilled with pollen or insecticide, in which case the holding tank is provided with a pair of covers coupled to the top end and cylindrical bottom end thereof, the covers being removable so as to couple the holding tank to the cover cone and the sleeve cylinder of the device.

7. The device according to claim 1, further comprising a pollen separator, which comprises:

a conical sieve fabric bag having a wide top end and a narrow bottom end;

a conical fabric bag surrounding the conical sieve fabric bag;

a pollen receptacle coupled to the bottom end of the non-permeable conical fabric bag;

a flexible cable disposed within the conical fabric bag, an upper end of the cable being provided with a handle, and a lower end of the cable being coupled to a ball disposed inside the fabric bag.

8. The device according to claim 1, further comprising an electrical grinding device adapted to grind male flowers so as to remove remaining pollens remaining therein, the grinding device being couplable to a pollen separator bag.

9. The device according to claim 1, further comprising a carrying bag closable by a zipper, wherein the carrying bag is provided with carrying handles and separate receptacles for holding the telescopic carrying pipe, pollen boxes, the dispensing tube, a rubber seal, a battery charger, charging cables, a pollen separation system, one or more pollen tanks, and a brush.

* * * * *